(12) United States Patent
Motojima et al.

(10) Patent No.: US 6,333,408 B1
(45) Date of Patent: Dec. 25, 2001

(54) OLIGONUCLEOTIDES INHIBITORS OF PAI-1 MRNA

(75) Inventors: Masaru Motojima, Saitama; Takao Ando, Yamanashi, both of (JP)

(73) Assignee: Kureha Chemical Industry Co., Ltd., Tokyo (JP)

( * ) Notice: Subject to any disclaimer, the term of this patent is extended or adjusted under 35 U.S.C. 154(b) by 0 days.

(21) Appl. No.: 09/521,617

(22) Filed: Mar. 8, 2000

(30) Foreign Application Priority Data

Mar. 8, 1999 (JP) .................................................. 11-060550

(51) Int. Cl.⁷ .................................................. C07K 21/00
(52) U.S. Cl. ...................... 536/24.5; 536/23.1; 536/24.3; 536/24.31; 536/24.33
(58) Field of Search .................................. 536/23.1, 24.3, 536/24.5; 514/44; 435/6, 325, 375

(56) References Cited

FOREIGN PATENT DOCUMENTS

WO95/19987 * 7/1995 (WO) .

OTHER PUBLICATIONS

Keeton et al., The Journal of Biological Chemistry, 1991 266:23048–23052, 1991 "Identification of Regulatory Sequences in the Type I Plasminogen Activator Inhibitor Gene Responsive to Transforming Growth Factor β*" (vol. 266 No. 34, issue of Dec. 5).

Dennler et al., The EMBO Journal vol. 17: No. 11 pp. 3091–3100 "Direct Binding of Smad3 and Smad4 to critical TGFβ–inducible elements in the promoter of human plasminogen activator inhibitor–type 1 gene" (1988).

Maeshima et al., "Inhibition of Mesangial Cell Proliferation by E2F Decoy Oligodeoxynubleotide In Vitro and In Vivo" J. Clin. Invest. 101:2589–2597 (1998).

Morishita et al., "A gene therapy strategy using a transcription factor decoy of the E2F binding site inhibits smooth muscle proliferation in vivo" Proc. Natl. Acad. Sci. USA vol. 92:5855–5859 (Jun. 1995).

Andrea D. Branch, A good antisense molecule is hard to find, TIBS, 47–48, Feb. 1998.*

Stanley Crooke, Antisense Research and Applications, Chapter 1, Basic Principles of Antisense Therapeutics, Springer–Verlag Press, Berlin, Heidelberg, New York, p. 3, Jul. 1998.*

* cited by examiner

Primary Examiner—John L. LeGuyader
Assistant Examiner—Janet L. Epps
(74) Attorney, Agent, or Firm—Sughrue Mion, PLLC

(57) ABSTRACT

An oligonucleotide containing a sequence of SEQ ID NO: 1: CAGTGAGTGG GTGGGGCTGG AACA, or SEQ ID NO: 2: TTAAGCTTTT ACCATGGTAA CCCC; a pharmaceutical composition comprising the oligonucleotide; and a method for treating or preventing a disease accompanied by an extracellular matrix deposition, are disclosed.

5 Claims, 1 Drawing Sheet

OLIGONUCLEOTIDES INHIBITORS OF PAI-1 MRNA

BACKGROUND OF THE INVENTION

1. Field of the Invention

The present invention relates to novel oligonucleotides, a pharmaceutical composition containing the oligonucleotide, and a method for inhibiting tissue fibrosis. The pharmaceutical composition of the present invention is useful for treating or preventing glomerulonephritis, glomerulosclerosis, interstitial fibrosis, pulmonary fibrosis, heart failure, cirrhosis, or angiitis.

2. Description of the Related Art

An extracellular matrix accumulation brings about glomerulosclerosis or interstitial fibrosis, which is a histological characteristic of progressive glomerular diseases, such as glomerulonephritis. The extracellular matrix forms a basement membrane or mesangial region of a glomerulus, and contains, for example, glycoproteins such as collagen, fibronectin, or laminin; or proteoglycans such as biglycan or decorin. The extracellular matrix regulates the functions of constituent cells in a normal glomerulus, but is increased upon the occurrence of glomerulonephritis or glomerulosclerosis, and is associated with a progress of nephritis.

According to recent findings, plasmin is known as one of the major factors regulating a turnover of the extracellular matrix in the mesangial cells. The formation of the plasmin is regulated by a balance between a plasminogen activator and various plasminogen activator inhibitors (PAIs). It is known that, in a glomerulus isolated from an animal model having proliferative glomerulonephritis, the accumulation of plasminogen activator inhibitor type 1 (PAI-1) to the extracellular matrix is increased. This suggests that PAI-1 is one of the key factors involved in the extracellular matrix accumulation in the mesangial cells. Namely, it is surmised that, when an amount of PAI-1 expressed is increased, the formation of plasmin, which is a protease, is inhibited, and as a result, the degradation of the extracellular matrix is inhibited. That is, it is surmised that, if the expression of PAI-1 can be inhibited, the extracellular matrix accumulation can be inhibited, and thus the tissue fibrosis can be prevented.

Therefore, it is expected that a compound capable of inhibiting the expression of PAI-1 is useful for treating or preventing diseases accompanied by an extracellular matrix deposition, such as glomerulonephritis, glomerulosclerosis, interstitial fibrosis, pulmonary fibrosis, heart failure, cirrhosis, or angiitis.

It is reported that each of angiotensin II and TGF-β increases an expression of PAI-1 mRNA in specific cells by itself, respectively. Further, it is known that some compounds can inhibit the PAI-1 mRNA expression induced by an action of one of angiotensin II or TGF-β. For example, Endocrinology, 130 (3), 1255–1262 (1992) discloses that angiotensin II increases the PAI-1 mRNA expression in an astroglia from a rat brain, and the induced expression of PAI-1 mRNA is inhibited by treating with a very high concentration of H-7, i.e., 1-(5-isoquinolinesulfonyl)-2-methylpiperazine, which is an inhibitor of protein kinase C. Further, Mol. Cell. Biol., 12 (1), 261–265 (1992) discloses that TGF-β1 increases the PAI-1 mRNA expression in epithelial cells of an MvILu lung, and the induced expression of PAI-1 mRNA is inhibited by the above H-7. J. Clin. Invest., 95 (3), 1353–1362 (1995) discloses that angiotensin II increases the PAI-1 mRNA expression in rat aortic smooth muscle cells and vascular endothelial cells, and the induced expression of PAI-1 mRNA in the vascular endothelial cells is partially inhibited by a genistein, i.e., a tyrosine kinase inhibitor. Furthermore, Kidney Int., 51 (3), 664–671 (1997) discloses that angiotensin II increases the PAI-1 mRNA expression in rat mesangial cells.

The above literatures disclose only compounds which may inhibit the PAI-1 mRNA expression induced by only one of angiotensin II or TGF-β.

In the process for investigating compounds capable of inhibiting the PAI-1 mRNA expression, the inventors of the present invention found that, in rat kidney mesangial cells, the PAI-1 mRNA expression induced by a signal from angiotensin II is synergistically increased by an action of TGF-β; that is, the PAI-1 mRNA expression is superinduced by subjecting the rat kidney mesangial cells to a treatment with angiotensin II and TGF-β at the same time, and disclosed the above findings in Japanese Patent Application No. 9-322125, which was laid-open on May 25, 1999 under Japanese Unexamined Patent Publication (Kokai) No. 11-139974. It is surmised that the PAI-1 mRNA expression induced by the simultaneous actions of angiotensin II and TGF-β is closer to the conditions in a living body, in comparison with the expression systems disclosed in the above literatures wherein the PAI-1 mRNA expression is induced by only one of angiotensin II or TGF-β.

Further, the present inventors found that genistein compounds or bisindolylmaleimide compounds having specific structures inhibit not only the PAI-1 mRNA superinduction by the simultaneous actions of angiotensin II and TGF-β, but also the PAI-1 mRNA induction by one of angiotensin II or TGF-β, and disclosed the above findings in Japanese Patent Application No. 9-322125. Therefore, it is expected that the compounds disclosed in Japanese Patent Application No. 9-322125 may inhibit the extracellular matrix accumulation more effectively than the inhibitors disclosed in the above literatures.

SUMMARY OF THE INVENTION

To obtain novel compounds capable of inhibiting the PAI-1 expression, the present inventors used a screening method by which the genistein and bisindolylmaleimide compounds were found as disclosed in Japanese Patent Application No. 9-322125. As a result, the present inventors found that compounds having structures entirely different from those of the genistein and bisindolylmaleimide compounds inhibit the PAI-1 mRNA superinduction by the simultaneous actions of angiotensin II and TGF-β. The present invention is based on these findings.

Accordingly, the object of the present invention is to provide novel compounds capable of inhibiting the PAI-1 mRNA superinduction.

Another object of the present invention is to provide a pharmaceutical composition useful for inhibiting tissue fibrosis.

Still another object of the present invention is to provide a pharmaceutical composition useful for treating or preventing diseases accompanied by extracellular matrix deposition, such as glomerulonephritis, glomerulosclerosis, interstitial fibrosis, pulmonary fibrosis, heart failure, cirrhosis, or angiitis.

Still another object of the present invention is to provide a method for treating or preventing diseases accompanied by extracellular matrix deposition, such as glomerulonephritis, glomerulosclerosis, interstitial fibrosis, pulmonary fibrosis, heart failure, cirrhosis, or angiitis.

Other objects and advantages of the present invention will be apparent from the following description.

In accordance with the present invention, there is provided an oligonucleotide containing a sequence of SEQ ID NO: 1 or SEQ ID NO: 2.

Further, in accordance with the present invention, there is provided a pharmaceutical composition comprising the oligonucleotide containing the sequence of SEQ ID NO: 1 or SEQ ID NO: 2 and a pharmaceutically or veterinarily acceptable carrier.

Still further, in accordance with the present invention, there is provided a method for inhibiting tissue fibrosis, comprising administering to a subject in need thereof the oligodeoxynucleotide containing the sequence of SEQ ID NO: 1 or SEQ ID NO: 2 in an amount effective therefor.

Still further, in accordance with the present invention, there is provided a method for treating or preventing diseases accompanied by extracellular matrix deposition, such as glomerulonephritis, glomerulosclerosis, interstitial fibrosis, pulmonary fibrosis, heart failure, cirrhosis, or angiitis, comprising administering to a subject in need thereof the oligonucleotide containing the sequence of SEQ ID NO: 1 or SEQ ID NO: 2 in an amount effective therefor.

DESCRIPTION OF THE PREFERRED EMBODIMENTS

Figure 1:
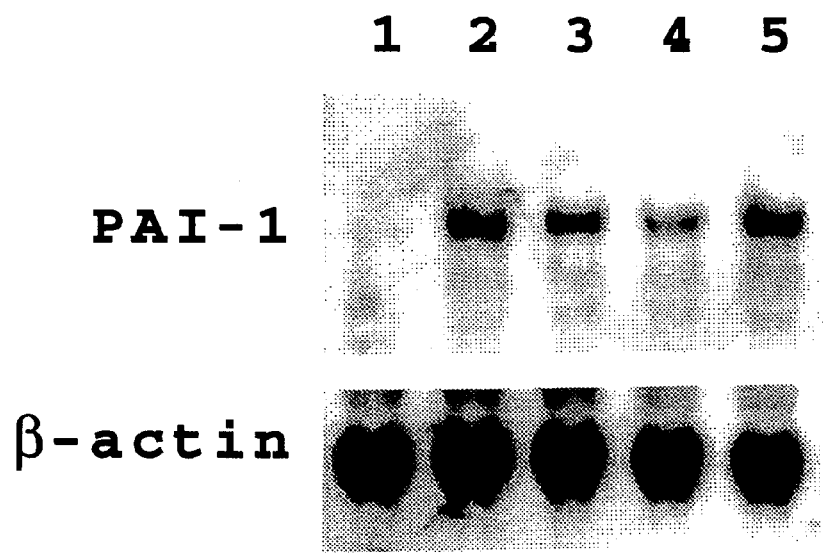
FIG. 1 illustrates the results of Northern blotting analysis conducted to confirm an inhibitory effect of oligonucleotide ODN-1 on the PAI-1 mRNA expression induced by angiotensin II and TGF-$\beta$1.

The present invention will be explained in detail hereinafter.

The oligonucleotide of the present invention comprises the sequence of SEQ ID NO: 1 or SEQ ID NO: 2. The term "oligonucleotide" as used herein means an oligodeoxyribonucleotide. The oligonucleotide of the present invention is preferably a double-stranded DNA, i.e., an isolated double-stranded DNA. The double-stranded DNA may be an oligonucleotide comprising the double-stranded DNA region of the sequence of SEQ ID NO: 1 or SEQ ID NO: 2. The oligonucleotide containing the double-stranded DNA region of the sequence of SEQ ID NO: 1 or SEQ ID NO: 2 may be, for example, (1) a double-stranded oligonucleotide consisting of or comprising a double-stranded DNA formed from a plus strand of the sequence of SEQ ID NO: 1 or SEQ ID NO: 2 and a minus strand of a sequence complementary to the sequence of SEQ ID NO: 1 or SEQ ID NO: 2;

(2) a hairpin-type oligonucleotide, i.e., an oligonucleotide comprising an oligonucleotide region (a plus strand region) having the sequence of SEQ ID NO: 1 or SEQ ID NO: 2, an oligonucleotide region capable of forming a loop region, and an oligonucleotide region (a minus strand region) having the sequence complementary to the sequence of SEQ ID NO: 1 or SEQ ID NO: 2 so that the plus strand region, the loop region and the minus strand region are linearly arranged in this sequential order, and a stem region is formed by the plus strand region and the minus strand region; and (3) a dumbbell-type oligonucleotide, i.e., an oligonucleotide comprising an oligonucleotide region (a plus strand region) having the sequence of SEQ ID NO: 1 or SEQ ID NO: 2, an oligonucleotide region capable of forming a first loop region, an oligonucleotide region (a minus strand region) having the sequence complementary to the sequence of SEQ ID NO: 1 or SEQ ID NO: 2, and an oligonucleotide region capable of forming a second loop region so that the plus strand region, the first loop region, the minus strand region, and the second loop region are cyclically arranged in this sequential order, and a stem region is formed from the plus strand region and the minus strand region.

When the oligonucleotide of the present invention is the double-stranded oligonucleotide (1), the number of bases contained in the plus or minus strand is not particularly limited, so long as the number of bases is not less than 24, i.e., the number of bases in the sequence of SEQ ID NO: 1 or SEQ ID NO: 2. The number of bases is preferably not more than the number of bases contained in the oligonucleotide which can permeate a cell membrane or a nuclear membrane, that is, generally 40 bases or less, more preferably 30 bases or less.

When the oligonucleotide of the present invention is the hairpin-type oligonucleotide (2) or the dumbbell-type oligonucleotide (3), the number of bases in the stem region, i.e., the number of bases in the plus strand region or the minus strand region, is not particularly limited, so long as the number of bases is not less than 24, i.e., the number of bases of the sequence of SEQ ID NO: 1 or SEQ ID NO: 2. The number of bases of stem region of the hairpin-type oligonucleotide (2) or the dumbbell-type oligonucleotide (3) is preferably not more than the number of bases contained in the hairpin-type or dumbbell-type oligonucleotide which can permeate a cell membrane or a nuclear membrane, that is, generally 40 bases or less, more preferably 30 bases or less. The number of bases in the loop region is generally 3 to 15 bases, more preferably 3 to 8 bases, from the standpoint of a resistance to a nuclease.

In the oligonucleotide of the present invention, internucleotide bonds between nucleosides may be independently a phosphodiester bond or a modified phosphodiester bond. The modified phosphodiester may be, for example, a methylphosphonate type bond wherein one of two non-crosslinked oxygen atoms in the phosphodiester bond is replaced with a methyl group; a phosphoramidate type bond wherein one of two non-crosslinked oxygen atoms in the phosphodiester bond is replaced with an amino group or a substituted amino group; a phosphorothioate type bond wherein one of two non-crosslinked oxygen atoms in the phosphodiester bond is replaced with a sulfur atom; or a phosphorodithioate type bond wherein each of two non-crosslinked oxygen atoms in the phosphodiester bond is replaced with a sulfur atom. The oligonucleotide of the present invention may contain one or more modified phosphodiester bonds as above in one or more internucleotide bonds. The modified phosphodiester bond is preferable as the internucleotide bond, from the standpoints of the specificity in molecular recognition, a stability of the double-stranded chain, a resistance to a nuclease, a penetrating property through a cell membrane, a low cytotoxicity, a moderate metabolizability, an easy procedure for preparation, and so on. Further, the phosphorothioate type bond is more preferable from the standpoint of a stability in a living body. It is particularly preferable that not less than half, or in particular all, of the internucleotide bonds are the modified phosphodiester bonds, in particular the phosphorothioate type bonds.

The oligonucleotide of the present invention may be prepared in accordance with methods which are in themselves known.

For example, the hairpin-type oligonucleotide or dumbbell-type oligonucleotide of the present invention may be prepared by, for example, a conventional phosphodiester or phosphotriester method, such as an H-phosphonate method, or by an automated DNA synthesizer of a phosphoramidite method, except for the sites to which the phosphorothioate bonds are incorporated.

The oligonucleotide containing the phosphorothioate bonds may be prepared, for example, using a 15% N,N,N',N'-tetraethylthiuram disulfide/acetonitrile solution instead of a water/iodine/pyridine solution, which is an oxidizing agent used in a conventional method for preparing a polynucleotide.

The double-stranded oligonucleotide composed of the plus strand and the minus strand may be prepared by synthesizing each of the plus strand and the minus strand, respectively, and annealing them.

The pharmaceutical composition of the present invention comprises the oligonucleotide containing the sequence of SEQ ID NO: 1 or SEQ ID NO: 2 and a pharmaceutically or veterinarily acceptable carrier or diluent. The oligonucleotide contained in the pharmaceutical composition of the present invention may be the oligonucleotide per se (without any additive), or preferably in the form of a complex with one or more liposomes or macromolecular micelles. The oligonucleotide of the present invention may be administered to an animal, preferably a mammal, particularly a human, optionally together with a pharmaceutically or veterinarily acceptable carrier or diluent, or optionally in the form of the complex with one or more liposomes or macromolecular micelles.

The liposome used in the present invention may be prepared, for example, from lipid molecules, such as phospholipid, glycolipid, or cholesterol, and may be a unilamellar or multilamellar liposome.

A phospholipid which may be used to prepare the liposome is, for example, a glycerophospholipid, such as phosphatidylcholine, phosphatidylethanolamine, phosphatidylserine, phosphatidic acid, phosphatidylglycerol, phosphatidylinositol, or cardiolipin, or a sphingophospholipid, such as sphingomyelin, ceramidephosphoryl ethanolamine, or ceramidephosphorylglycerol. A glycolipid which may be used to prepare the liposome is, for example, a glyceroglycolipid, such as digalactosyldiglyceride or seminolipid, or sphingoglycolipid, such as galactosylceramide, or lactosylceramide.

The liposome is classified into a neutral liposome, a cationic liposome, an anionic liposome, a pH sensitive liposome and so forth, on the basis of a charged state of a polar portion thereof. In the present invention the cationic liposome is preferable, because the oligonucleotide, which is another part of the complex, is negatively charged and a surface of a cell is also negatively charged.

The cationic liposome is, for example, a synthesized mixture of a cationic head lipid and a helper lipid. For example, a cationic liposome used in the present invention may be prepared from (1) (a) a monocationic head, such as N-[1-(2,3-dioleyloxy)propyl]-N,N,N-triethylammonium (DOTMA), N-[1-(2,3-dimyristyloxy)propyl]-N,N-dimethyl-N-(2-hydroxyethyl)ammoniumbromide (DMRIE), 1,2-dioleyloxy-3-(triethylammonio)propane (DOTAP), dimethyldioctadecylammoniumbromide (DDAB), 3β-[N-(N',N'-dimethylaminoethane)-carbamoyl]cholesterol (PC-cholesterol), or 1-[2-9(Z)-octadecenoyloxy)-ethyl-2-(8(Z)-heptadecenyl)-3-(2-hydroxyethyl)-imidazolinium chloride (DOTIM), or (b) a polycationic head, such as, dioctadecylamideglycylspermine (DOGS) or 2,3-dioleyloxy-N-[2-(sperminecarboxamide)ethyl]-N,N-dimethyl-1-propaneammoniumtrifluoroacetate (DOSPA); and (2) a helper lipid, such as, dioleoyl-phosphatidylethanolamine (DOPE) or dioleylphosphatidylcholine (DOPC).

The forms of the oligonucleotide and the liposome in the complex to be administered are not particularly limited, so long as the oligonucleotide and the liposome are contained in the complex at the same time. The complex may be, for example, a mixture of the oligonucleotide and the liposome, or an embedded or encapsulated form of the oligonucleotide with the liposome, the embedded complex being preferable. The complex may be prepared, for example, in accordance with a method for forming the complex of the oligonucleotide and the liposome by an electrostatic bond, that is, a lipofection method wherein the oligonucleotide and the liposome are slowly mixed in a test tube and then allowed to stand.

The embedded complex may be prepared, for example, by a method for embedding the oligonucleotide of the present invention in the liposome. More particularly, a lipid, such as phosphatidylserine, is used to form a multilamellar liposome by a vortex mixer or the like, and then the multilamellar liposome is treated by ultrasonication to form a unilamellar liposome. The oligonucleotide is added to the resulting unilamellar liposome. Thereafter, the whole is lightly treated by a vortex mixer or the like, and then incubated at about 37° C. for about 10 minutes, or lyophilized and rehydrated to obtain the embedded complex. The encapsulated complex may be prepared by a known method.

The macromolecular micelle which may be used in the present invention is, for example, an electrostatically bonded macromolecular micelle formed from a block copolymer containing non-charging segments and charging segments.

The non-charging segment in the electrostatically bonded macromolecular micelle may be, for example, a segment stemming from a polyalkylene glycol, such as polyethylene glycol or polypropylene glycol, a polyalkylene oxide, a polysaccharide, a polyacrylamide, a substituted polyacrylamide, a polymethacrylamide, a substituted polymethacrylamide, a polyvinyl pyrrolidone, a polyvinyl alcohol, a polyacrylate, a polymethacrylate, or a polyamino acid, or a derivative thereof.

The charging segment in the electrostatically bonded macromolecular micelle may be, for example, a segment stemming from a polyamino acid having charging sidechains, more particularly, polyaspartic acid, polyglutamic acid, polylysine, polyarginine, or polyhistidine, polymalic acid, polyacrylic acid, polymethacrylic acid, polyethyleneimine, polyvinylamine, polyallylamine, or polyvinylimidazole, or a derivative thereof.

The block copolymer of the non-charging segments and the charging segments may be, for example, a polyethylene glycol-polyaspartic acid block copolymer, a polyethylene oxide-polyglutamic acid block copolymer, a polyethylene glycol-polyarginine block copolymer, a polyethylene glycol-polyhistidine block copolymer, a polyethylene glycol-polymethacrylic acid block copolymer, a polyethylene glycol-polyethyleneimine block copolymer, a polyethylene glycol-polyvinylamine block copolymer, a polyethylene glycol-polyallylamine block copolymer, a polyethylene oxide-polyaspartic acid block copolymer, a polyethylene oxide-polyglutamic acid block copolymer, a polyethylene oxide-polylysine block copolymer, a polyethylene oxide-polyacrylic acid block copolymer, a polyethylene oxide-polyvinylimidazole block copolymer, a polyacrylamide-polyaspartic acid block copolymer, a polyacrylamide-polyhistidine block copolymer, a polymethacrylamide-polyacrylic acid, a polymethacrylamide-polyvinylamine block copolymer, a polyvinyl pyrrolidone-polymethacrylic acid block copolymer, a polyvinyl alcohol-polyaspartic acid block copolymer, a polyvinyl alcohol-polyarginine block copolymer, a polyacrylate-polyglutamic acid block copolymer, a polyacrylate-polyhistidine block copolymer, a polymethacrylate-polyvinylamine block copolymer, or a polymethacrylic acid-polyvinylimidazole block copolymer.

The forms of the oligonucleotide and the macromolecular micelle in the complex to be administered are not particularly limited, so long as the oligonucleotide and the macromolecular micelle are contained in the complex at the same time. The complex may be, for example, a mixture of the oligonucleotide and the macromolecular micelle, or an embedded form of the oligonucleotide with the macromolecular micelle, the embedded complex being preferable.

The oligonucleotide of the present invention may be carried on the macromolecular micelle basically by mixing the oligonucleotide with the block copolymer or a solution thereof. Further, in addition to the mixing procedure, a dialysis, a stirring, a diluting, concentrating, or ultrasonic treatment, or a temperature or pH controlling, and/or an addition of an organic solvent may be carried out, if necessary.

For example, the oligonucleotide of the present invention may be carried on the polyethylene glycol-polylysine block copolymer by mixing a solution of the oligonucleotide with an aqueous solution of the copolymer under the conditions of an appropriate ratio, ionic strength, pH and so on. The complex of the oligonucleotide and the macromolecular micelle can have a stable macromolecular micelle structure, and effectively incorporate the charging oligonucleotide. Further, the oligonucleotide of the present invention can be administered into a body in a stable form, when the complex of the oligonucleotide and the macromolecular micelle is used.

The formulation of the pharmaceutical composition of the present invention is not particularly limited to, but may be, for example, oral medicines, such as powders, fine subtilaes, granules, tablets, capsules, suspensions, emulsions, syrups, extracts or pills, or parenteral medicines, such as injections, liquids for external use, ointments, suppositories, creams for topical application, or eye lotions.

The oral medicines may be prepared by an ordinary method using, for example, fillers, binders, disintegrating agents, surfactants, lubricants, flowability-enhancers, diluting agents, preservatives, coloring agents, perfumes, tasting agents, stabilizers, humectants, antiseptics, antioxidants, or the like, such as gelatin, sodium alginate, starch, corn starch, saccharose, lactose, glucose, mannitol, carboxylmethylcellulose, dextrin, polyvinyl pyrrolidone, crystalline cellulose, soybean lecithin, sucrose, fatty acid esters, talc, magnesium stearate, polyethylene glycol, magnesium silicate, silicic anhydride, or synthetic aluminum silicate.

For the parenteral administration, for example, an injection such as a subcutaneous or intravenous injection, or the per rectum administration, may be used. Of the parenteral formulations, an injection is preferably used.

When the injections are prepared, for example, water-soluble solvents, such as physiological saline or Ringer's solution, water-insoluble solvents, such as plant oil or fatty acid ester, tonicity agents, such as glucose or sodium chloride, solubilizing agents, stabilizing agents, antiseptics, suspending agents, emulsifying agents or the like may be optionally used, in addition to the oligonucleotide of the present invention.

The pharmaceutical composition may be administered in the form of a sustained release preparation using sustained release polymers. For example, the pharmaceutical composition of the present invention may be incorporated into a pellet made of ethylenevinyl acetate polymers, and the pellet may be surgically implanted in a tissue to be treated.

The pharmaceutical composition of the present invention may contain the oligonucleotide of the present invention in an amount, but not particularly limited to, of 0.01 to 99% by weight, preferably 0.1 to 80% by weight.

When the pharmaceutical composition of the present invention is utilized, the dose is not particularly limited, but varies with the kind of disease, the age, sex, body weight, or symptoms of the subject, a method of administration, or the like. However, the oligonucleotide of the present invention may be orally or parenterally administered.

The pharmaceutical composition of the present invention may be used not only for the pharmaceutical application but also for various applications. That is, the oligonucleotide of the present invention may be administered in the form of functional food or healthy food, or a feed, together with a conventional food additive, or directly added to food as a food additive.

As explained, the oligonucleotide containing the sequence of SEQ ID NO: 1 or SEQ ID NO: 2 according to the present invention can inhibit the PAI-1 mRNA expression in cells. Therefore, the pharmaceutical composition comprising the oligonucleotide of the present invention is useful for inhibiting the PAI-1 mRNA expression.

When the oligonucleotide containing the sequence of SEQ ID NO: 1 or SEQ ID NO: 2 according to the present invention is administered, the PAI-1 mRNA expression in the cells treated with angiotensin II and TGF-$\beta$1 is reduced, and as a result, the activities of plasmin and plasminogen activator, i.e., proteases, are increased. Therefore, the degradation of the extracellular matrix is facilitated, and the accumulation of the extracellular matrix is inhibited.

Accordingly, the oligonucleotide containing the sequence of SEQ ID NO: 1 or SEQ ID NO: 2 according to the present invention can be used for treating or preventing diseases accompanied by the extracellular matrix deposition, such as glomerulonephritis, glomerulosclerosis, interstitial fibrosis, pulmonary fibrosis, heart failure, cirrhosis, or angiitis.

EXAMPLES

The present invention will now be further illustrated by, but is by no means limited to, the following Examples.

EXAMPLE 1

(1) Preparation of Rat Kidney Mesangial Cells

Kidney cortex was isolated from a 7 week-old male Sprague-Dawley rat, and was minced and passed through a series of sieves to isolate glomeruli. Isolated glomeruli were treated with 1 mg/ml collagenase for 30 minutes, and spread onto a 100 mm plastic tissue culture dish in an RPMI-1640 medium containing 17% fetal bovine serum, 0.1 U/ml insulin and antibiotics (50 U/ml penicillin and 50 $\mu$g/ml streptomycin). Outgrowing mesangial cells were maintained in the same medium and used in the following Examples at passages 6 to 9.

The expression of angiotensin II receptors was confirmed at each passage by the following $^{125}$I-angiotensin II binding assay. More particularly, rat mesangial cells were seeded onto a 24 well culture plate at a density of 1×10⁵ cells/well. The cells were incubated in a buffer containing 50 mM Tris-HCl (pH 7.5), 2.5 mM $MgCl_2$, 0.1% bovine serum albumin (BSA), 100 μM bacitracin and 50 pM [$^{125}$I] angiotensin II (Shigma) at 37° C. for 1 hour. Then the cells were washed twice with ice-cold phosphate-buffered saline (PBS) and dissolved in 0.25N NaOH containing 0.1% sodium dodecyl sulfate (SDS). The radioactivity in the lysate was counted by a gamma counter, to determine an amount of the angiotensin II receptors expressed in the rat mesangial cells. Nonspecific binding was determined in the presence of 10 μM non-labeled angiotensin II.

(2) Inhibitory Effect by the Oligonucleotides (Double-stranded DNAs)

Hereinafter, the effect of the oligonucleotides (double-stranded DNAs) according to the present invention on inhibiting the plasminogen activator inhibitor type 1 (PAI-1) mRNA expression induced by angiotensin II and TGF-β1 was confirmed.

As the oligonucleotides according to the present invention, the double-stranded DNA of the sequence of SEQ ID NO: 1 wherein all of the internucleoside bonds are phosphorothioate bonds (hereinafter referred to as the oligonucleotide ODN-1), and the double-stranded DNA of the sequence of SEQ ID NO: 2 wherein all of the internucleoside bonds are phosphorothioate bonds (hereinafter referred to as the oligonucleotide ODN-2) were used. Comparative oligonucleotides used were a double-stranded DNA wherein the 10th to 14th sequence "GGTGG" in the oligonucleotide ODN-1 was replaced with "AATTC" wherein all of the internucleoside bonds are phosphorothioate bonds (hereinafter referred to as the oligonucleotide c-ODN-1), and a double-stranded DNA wherein the 11th to 13th sequence "ACC" in the oligonucleotide ODN-2 was replaced with "CAA" wherein all of the internucleoside bonds are phosphorothioate bonds (hereinafter referred to as the oligonucleotide c-ODN-2). The above oligonucleotides were prepared by an automated DNA synthesizer.

The rat mesangial cells (1×10⁶) prepared as in Example 1 (1) were incubated in 5 ml of RPMI-1640 medium containing 0.1 U/ml insulin and antibiotics (50 U/ml penicillin and 50 μg/ml streptomycin) for 24 hours, to make the cells into a stationary phase. The oligonucleotide according to the present invention, i.e., the oligonucleotide ODN-1 or the oligonucleotide ODN-2, was added to the rat mesangial cells in the stationary phase, so that a concentration of the oligonucleotide became 1 μM or 5 μgM, and the whole was incubated for 16 hours. Thereafter, angiotensin II (concentration=100 nM) and human recombinant TGF-β1 (concentration=10 ng/ml) were added, and the whole was incubated for 6 hours.

After the medium was removed, the cells were washed with Hanks' balanced salt solution, and the total RNA was isolated by a commercially available solution for isolating RNA (ISOGEN; Wako Pure Chemical Ind., Ltd.). The isolation was conducted in accordance with the instructions attached to the ISOGEN. Briefly, 1 ml of the RNA-isolating solution was added to the mesangial cells. After lysis of the cells, the resulting lysate was transferred to a tube, extracted with chloroform, and centrifuged to isolate an aqueous phase. RNAs in the aqueous phase were precipitated with isopropanol. The precipitated RNAs were rinsed with 75% ethanol, and then resuspended in a DEPC (diethylpyrocarbonate) treated water.

Subsequently, the resulting total RNA was used to determine an amount of the PAI-1 mRNA expression induced by angiotensin II and TGF-β1 in the rat mesangial cells, using Northern blotting.

More particularly, the total RNA (about 10 to 20 μg) was electrophoresed on 1% agarose formaldehyde gel. The fractionated RNA was transferred from the gel to a nylon membrane (Hybond N+ nylon membrane; Amersham), and immobilized by UV cross-linking. The membrane was pre-hybridized in a solution containing 4×SSCP, 1×Denhard't, 1% SDS, 50% formamide, and 100 μg/ml salmon sperm DNA at 42° C. for 3 hours. 1×SSCP means an aqueous solution containing 0.12 M NaCl, 0.015 M sodium citrate, and 0.015 M $Na_2HPO_4$, and 0.005 M-$NaH_2PO_4$, and 1×Denhard't means a solution containing 0.02% ficoll, 0.02% polyvinyl pyrrolidone, and 0.02% BSA.

Hybridization was performed in a solution containing 4×SSCP, 1×Denhard't, 1% SDS, 5% dextran sulfate, 50% formamide, 100 μg/ml salmon sperm DNA, and a denatured probe labeled with digoxigenin (DIG), at 42° C. for 16 hours. The probe used for detecting PAI-1 mRNA was a rat PAI-1 cDNA fragment containing the 345th to 1221st sequence. The probe used for detecting β-actin mRNA was a rat β-actin mRNA cDNA fragment containing the 945th to 1428th sequence. The cDNA fragments were labeled with a commercially available DIG labeling kit (DIG high prime; Boehringer Mannheim) in accordance with the instructions attached to the kit.

After hybridization, the membrane was washed twice with 1×SSC containing 0.1% SDS at room temperature for 15 minutes, and then twice with 0.2×SSC containing 0.1% SDS at 42° C. for 15 minutes. 1×SSC means a solution containing 0.15 M NaCl and 0.015 M sodium citrate. Thereafter, the hybridized probe was detected with a DIG detection kit in accordance with the instructions attached to the kit.

As Comparative Examples, the above procedures were repeated except that, instead of the oligonucleotides of the present invention, the comparative oligonucleotides, i.e., the oligonucleotide c-ODN-1 or oligonucleotide c-ODN-2, were added at the concentration of 5 μm, or neither of the oligonucleotides were added. Further, as a Control Example, the above procedures were repeated except that the oligonucleotides of the present invention, angiotensin II and human recombinant TGF-β1 were not added.

Figure 2:
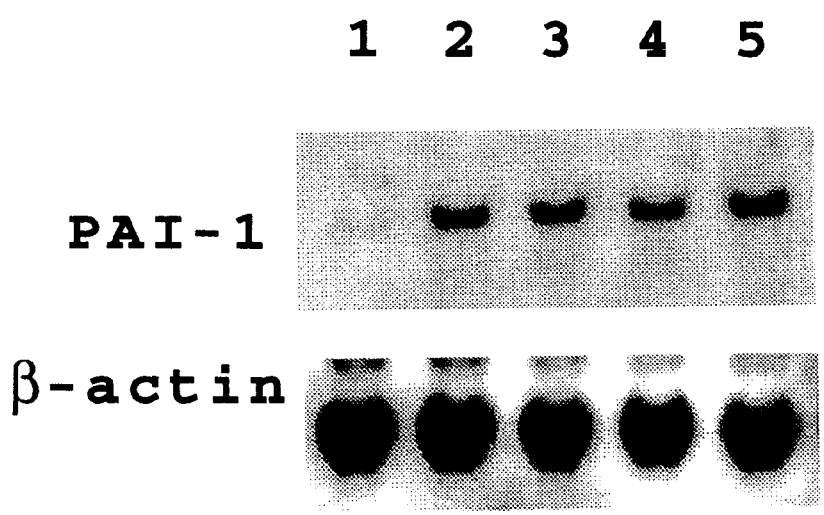
FIG. 2 illustrates the results of Northern blotting analysis conducted to confirm an inhibitory effect of oligonucleotide ODN-2 on the PAI-1 mRNA expression induced by angiotensin II and TGF-$\beta$1.

FIG. 1 shows the results obtained from the oligonucleotide ODN-1 of the present invention, and the comparative oligonucleotide c-ODN-1. FIG. 2 shows the results obtained from the oligonucleotide ODN-2 of the present invention, and the comparative oligonucleotide c-ODN-2.

In FIG. 1, lane 1 shows the results of the Control Example; lane 2 shows the results of the case wherein the oligonucleotide was not added, but angiotensin II and human recombinant TGF-β1 were added; lanes 3 and 4 show the results of the cases wherein the oligonucleotide ODN-1 was added so that the concentration thereof became 1 μM or 5 μM, and tensin II and human recombinant TGF-β1 were added; and lane 5 shows the results of the case wherein the oligonucleotide c-ODN-1 was added so that the concentration thereof became 5 μM, and angiotensin II and human recombinant TGF-β1 were added. The relationship between lanes in FIG. 1 and the compounds added is shown in Table 1. In Table 1, "AngII" means angiotensin II.

As apparent from FIG. 1, the oligonucleotide ODN-1 of the present invention inhibited the PAI-1 mRNA induction by angiotensin II and TGF-β1 in a concentration-dependent manner. Specifically, when the concentration of the oligonucleotide ODN-1 was 1 μM, the inhibition of 16±3% was observed, and when the concentration of the oligonucleotide ODN-1 was 5 μM, the inhibition was 68±9%. No significant inhibition was observed in the comparative oligonucleotide c-ODN-1 (5 μM).

TABLE 1

| Lane | AngII + TGF-β1 | oligonucleotide |
|---|---|---|
| 1 | not added | not added |
| 2 | added | not added |
| 3 | added | ODN-1 (1 μM) |
| 4 | added | ODN-1 (5 μM) |
| 5 | added | c-ODN-1 (5 μM) |

In FIG. 2, lane 1 shows the results of the Control Example; lane 2 shows the results of the case wherein the oligonucleotide was not added, but angiotensin II and human recombinant TGF-β1 were added; lanes 3 and 4 show the results of the cases wherein the oligonucleotide ODN-2 was added so that the concentration thereof became 1 μM or 5 μM, and ensin II and human recombinant TGF-β1 were added; and lane 5 shows the results of the case wherein the oligonucleotide c-ODN-2 was added so that the concentration thereof became 5 μM, and angiotensin II and human recombinant were added. The relationship between lanes in FIG. 2 and the compounds added is shown in Table 2. In Table 2, "AngII" means angiotensin II.

As apparent from FIG. 2, the oligonucleotide ODN-2 of the present invention inhibited the PAI-1 mRNA induction by tensin II and TGF-β1 in a concentration-dependent manner. Specifically, when the concentration of the oligonucleotide ODN-2 was 1 μM, the inhibition of 8±4% was observed, and when the concentration of the oligonucleotide ODN-2 was 5 μM, the inhibition was 36±10%. No significant inhibition was observed in the comparative oligonucleotide c-ODN-2 (5 μM).

TABLE 2

| Lane | AngII + TGF-β1 | oligonucleotide |
|---|---|---|
| 1 | not added | not added |
| 2 | added | not added |
| 3 | added | ODN-2 (1 μM) |
| 4 | added | ODN-2 (5 μM) |
| 5 | added | c-ODN-2 (5 μM) |

As explained, the oligonucleotide of the present invention inhibits the PAI-1 MRNA expression in the cells treated with angiotensin II and TGF-β1, and reduces biosynthesis of PAI-1. This suggests that the oligonucleotide of the present invention can increase the activities of plasmin and plasminogen activator, which are proteases, accelerate degradation of the extracellular matrix, and thus inhibit the extracellular matrix accumulation, and accordingly, inhibit the progress of the tissue fibrosis.

Although the present invention has been described with reference to specific embodiments, various changes and modifications obvious to those skilled in the art are deemed to be within the spirit, scope, and concept of the invention.

Sequence List
<110> Kureha Chemical Industry Co., Ltd.
<120> Novel Oligonucleotides, Pharmaceutical Composition and Method for Inhibiting Tissue Fibrosis
<130> KRH995621P
<160> 2
<210> 1
<211> 24
<212> DNA
<213> Artificial Sequence
<220>
<223> The oligonucleotide has a function to inhibit tissue fibrosis.
<400> 1
cagtgagtgg gtggggctgg aaca 24
<210> 2
<211> 24
<212> DNA
<213> Artificial Sequence
<220>
<223> The oligonucleotide has a function to inhibit tissue fibrosis.
<400> 2
ttaagctttt accatggtaa cccc 24

SEQUENCE LISTING

<160> NUMBER OF SEQ ID NOS: 2

<210> SEQ ID NO 1
<211> LENGTH: 24
<212> TYPE: DNA
<213> ORGANISM: Artificial Sequence
<220> FEATURE:
<223> OTHER INFORMATION: The oligonucleotide has a function to inhibit
      tissue fibrosis.

<400> SEQUENCE: 1
cagtgagtgg gtggggctgg aaca                                          24

<210> SEQ ID NO 2
<211> LENGTH: 24
<212> TYPE: DNA
<213> ORGANISM: Artificial Sequence
<220> FEATURE:

-continued

```
<223> OTHER INFORMATION: The oligonucleotide has a function to inhibit
      tissue fibrosis.

<400> SEQUENCE: 2
ttaagctttt accatggtaa cccc                                            24
```

We claim:

1. An isolated double-stranded oligonucleotide consisting of a plus strand of a sequence of SEQ ID NO: 1 or SEQ ID NO: 2 and a minus strand of a sequence complementary to said sequence of SEQ ID NO: 1 or SEQ ID NO: 2.

2. An isolated hairpin oligonucleotide comprising a plus strand region having a sequence of SEQ ID NO: 1 or SEQ ID NO: 2, an oligonucleotide region capable of forming a loop region, and a minus strand region having a sequence complementary to said sequence of SEQ ID NO: 1 or SEQ ID NO: 2 so that said plus strand region, said loop region and said minus strand region are linearly arranged in this sequential order, and a stem region is formed by said plus strand region and said minus strand region.

3. The isolated hairpin oligonucleotide according to claim 2, wherein said plus strand region consists essentially of said sequence of SEQ ID NO: 1 or SEQ ID NO: 2, and said minus strand region consists essentially of the complement of the sequence of SEQ ID NO: 1 or SEQ ID NO:2.

4. An isolated dumbbell oligonucleotide comprising a plus strand region having a sequence of SEQ ID NO: 1 or SEQ ID NO: 2, an oligonucleotide region capable of forming a first loop region, a minus strand region having a sequence complementary to said sequence of SEQ ID NO: 1 or SEQ ID NO: 2, and an oligonucleotide region capable of forming a second loop region so that said plus strand region, said first loop region, said minus strand region, and said second loop region are cyclically arranged in this sequential order, and a stem region is formed from said plus strand region and said minus strand region.

5. The isolated dumbbell oligonucleotide according to claim 4, wherein said plus strand region consists essentially of said sequence of SEQ ID NO: 1 or SEQ ID NO: 2, and said minus strand region consists essentially of the complement of the sequence of SEQ ID NO: 1 or SEQ ID NO:2.

* * * * *